(12) United States Patent
Claudio

(10) Patent No.: US 7,560,439 B2
(45) Date of Patent: Jul. 14, 2009

(54) METHOD FOR INCREASING THE GENE EXPRESSION OF TRANSFECTED GENES

(75) Inventor: Pisano Claudio, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 595 days.

(21) Appl. No.: 10/949,194

(22) Filed: Sep. 27, 2004

(65) Prior Publication Data

US 2005/0124570 A1    Jun. 9, 2005

Related U.S. Application Data

(63) Continuation of application No. 10/203,924, filed as application No. PCT/IT01/00057 on Feb. 9, 2001, now abandoned.

(30) Foreign Application Priority Data

Feb. 17, 2000    (IT) ......................... RM2000A0077

(51) Int. Cl.
*A01N 43/04* (2006.01)
*C12N 15/00* (2006.01)
*C12P 21/04* (2006.01)
*C12N 5/00* (2006.01)

(52) U.S. Cl. ........................ 514/44; 435/455; 435/70.1; 435/375

(58) Field of Classification Search ................... 514/44; 435/455, 70.1, 375
See application file for complete search history.

(56) References Cited

U.S. PATENT DOCUMENTS 6,040,295 A    3/2000    Rolland et al.
6,465,007 B1 *    10/2002    Eastman et al. ............. 424/450

FOREIGN PATENT DOCUMENTS

WO    WO 99/07094    11/1999
WO    WO 99/56784    11/1999

OTHER PUBLICATIONS

Wang et al. J. Med. Chem. 41:2207-2215, 1998.*
Thomas et al. Nature Rev./Genet. 4: 346-358; 2003.*
Gadaleta et al, "Acetyl-L-Carnitine Increases Cytochrome Oxidase Subunit I Messenger RNA Content in Hypothyroid Rat Liver", FEBS (Federation of European Biochemical Societies) Letters, vol. 277, No. 1-2, 1990, pp. 191-193.
Deonarain (1998) Exp. Opin. Ther. Pat., 8(1):53-69.
Gorecki (2001) Exp. Opin. Emerging Drugs, 6(2):187-98.
Verma, et al. (1997) Nature, 389:239-42.
Eck, et al. (1996) Goodman & Gilman's The Pharmacological Basis of Therapeutics, 9th Ed., McGraw-Hill, New York, NY., pp. 77-101.
Short Protocols in Molecular Biology (1995) 3.d Ed., Wiley and Sons, New York, NY, p. 9-1.
Stryer (1988) Biochemistry, 3.d Ed., Freeman and Co., New York, NY., pp. 704, 716-717.

* cited by examiner

*Primary Examiner*—Fereydoun G Sajjadi
(74) *Attorney, Agent, or Firm*—Nixon & Vanderhye P.C.

(57) ABSTRACT

The present invention provides a method of increasing the gene expression of transfected genes which includes the administration of a carnitine.

3 Claims, No Drawings

METHOD FOR INCREASING THE GENE EXPRESSION OF TRANSFECTED GENES

The present application is a continuation of U.S. application Ser. No. 10/203,924, filed Aug. 16, 2002, now abandoned which is a 371 U.S. National Phase of International Application PCT/IT01/00057, filed 9 Feb. 2001, which claims benefit of IT RM2000A000077, filed 17 Feb. 2000, the entire contents of each of which is hereby incorporated by reference.

The invention described herein relates to the use of $C_1$-$C_6$ alkanoyl L-carnitines in particular acetyl L-carnitine, in the production of recombinant proteins.

The production of proteins by means of the genetic engineering technique, i.e. using cell clones in which genes are inserted by transfection, is known. One of the problems encountered in the use of transfected clones is that after a certain period of time the genes artificially inserted in the cell for the purpose of producing the desired protein become silent. The problem of the silencing of the genes is even more keenly perceived in gene therapy. In this case, the gene, which has been inserted in the patient, ceases to produce the therapeutically necessary protein.

It has now been found that $C_1$-$C_6$ alkanoyl L-carnitines and preferably acetyl L-carnitine, or L-carnitine, increases the gene expression of transfected genes.

What is meant by "a carnitine" for the purposes of this invention is a $C_1$-$C_6$ alkanoyl L-carnitine or L-carnitine. In the following description, purely by way of an example, reference is made to the preferred embodiment with acetyl L-carnitine.

Treatment with acetyl L-carnitine in cell clones transfected using known techniques, e.g. liposomes, considerably increases the expression of proteins coded for by the transfected genes.

It is an object of the present invention a method for increasing the gene expression of transfected genes comprising the administration of acetyl L-carnitine.

In its industrial applicability aspects, the invention described herein refers to the use of acetyl L-carnitine to increase the expression of recombinant proteins, along with a method for the production of recombinant proteins, the improvement in which consists in the use of acetyl L-carnitine to increase the expression of said proteins.

In the therapeutic sector and in the field of genetic engineering in general, the subject matter of the invention described herein is the use of acetyl L-carnitine for the preparation of a product useful in gene therapy for improving the expression of proteins, as well as the use of acetyl L-carnitine for the preparation of a product useful for maintaining transfected genes in clones.

The invention described herein is further illustrated by means of the experimental part presented here below.

Materials and Methods

In-vitro Experiments

Cell cultures. The uterine cervical carcinoma cell line HeLa, ATCC was used. The cells were cultured in RPMI 1640 Medium (eurobio), containing antibiotics and 10% foetal calf serum.

Treatment with acetyl-L-carnitine (ALC). $4 \times 10^6$ and $5 \times 10^6$ cells cultured in a medium containing ALC at final concentrations of 5 mM and 10 mM, respectively, were seeded in two 125 cm$^3$ flasks, whereas $2 \times 10^6$ cells not treated with ALC were plated in a 75 cm$^3$ flask. The treatment was repeated after 48 h (coinciding with the seeding of the cells for transfection) and after 72 h (at the end of transfection) and was also repeated after 120 h only in the case of samples transfected for lysis at 72 h.

Transient transfection of pRL-CMV plasmid. The cells were seeded for transfection 24 h before in 12-well plates (Corning), in amounts corresponding to $10^5$ cells per well. The transfection was carried out in triplicate for each sample using the liposome DOTAP (Boehringer-Mannheim, Indianapolis, Ind.) and the plasmid pRL-CMV (Promega cat. N° E2261). In brief, 1.5 μg/well of DNA and 9.2 μM/well of liposome were used per sample, considering a final volume of 1050 μl/sample; the transfection mixture (25 μl /sample) was left at ambient temperature for 30 min and then HBS 2× (20 mM HEPES, 150 mM NaCl, pH 7.4) was added in amounts of 25 μl/ sample, and 50 μl/sample of the solution thus obtained was added to the cells for 5 hours. After carrying out three washings with PBS (phosphate buffer pH 7.4) without calcium and magnesium, the cells were cultured in growth medium containing ALC at the concentrations indicated in the treatments up to the time of cell lysis for the luciferase assay. As a control, naked DNA was added in a 1× HBS solution.

Luciferase Assay in Transfected Samples in Vitro

The cells were washed with PBS (phosphate buffer pH 7.4) without calcium and magnesium and subjected to lysis by means of the addition of 200 μl of lysis buffer contained in the GeneLux L002-100 kit (Wallac) used for the luciferase assay. After 20 min, total proteins were collected and 10 μl of each sample were assayed for luciferase, following the procedures indicated in the kit; the assay was carried out in 96-multiwell plates using the Victor$^2$ luminometer (Wallac). The luminescence readings obtained, expressed in relative light units (RLU), were normalised for mg of total proteins, calculated using the Bradford Method.

In-vivo Experiments

Treatment with acetyl L-carnitine (ALC). The animals used for the in-vivo experiments were Balb/c (Harlan) mice, 5 animals per group. The groups were subdivided into untreated animals (3 groups) and treated animals (6 groups) treated with oral doses of 100 mg/kg of ALC]. The treatment was initiated four days prior to transfection with daily administrations and was repeated every day up to the time of sacrifice.

Sacrifice of Animals

The animals were sacrificed 24, 48 and 72 h after transfection.

The lungs were taken from each animal, washed in saline solution, weighed, frozen in liquid nitrogen and stored at −80° C. up to the time of protein extraction.

Transfection of pRL-CMV plasmid. The animals making up the untreated groups and three of the groups of animals treated with ALC received intravenous injections of 25 μg/mouse of pRL-CMV plasmid using a liposome at a concentration of 12 μm/μg of injected DNA. The liposome and the DNA were mixed in a solution of PBS and kept in ice for 1 h before injection. The other three groups of treated animals received injections of 25 μg/mouse of pRL-CMV plasmid in a solution consisting of PBS alone. The final volume of injected solution in each animal was 208 μl.

Extraction of Proteins from Lungs and Luciferase Assay

Results

Luciferase expression in transfection in vitro

Lysates at 24 h. The expression of luciferase obtained in the samples treated with ALC was higher than in samples of untreated cells. The mean RLU value per mg of total proteins, calculated on the basis of the samples in triplicate, showed an approximately 1.6-fold increase in the samples treated with 5 mM ALC as compared to the untreated samples. In addition, it was observed that, in the samples treated with 10 mM ALC, there was no additional increase. The results obtained appear to indicate the absence of a dose-dependent relationship between ALC and luciferase expression, at least at the concentrations used in our experiment, whereas they do indicate a positive effect on the expression of transfected luciferase. In the samples transfected with DNA alone, which constituted our control group, no luciferase activity was observed.

Lysates at 48 h. The effect observed in the samples subjected to lysis at 24 h was not maintained 48 h after transfection, where, however, luciferase expression diminished in absolute terms in all transfected samples. The RLUs obtained per mg of proteins show no significant differences between treated and untreated samples.

Lysates at 72 h. The samples present no luciferase expression, in that significant RLU/mg values cannot be determined.

Expression of Luciferase in Vivo.

Experiment 2 HeLa 100000/12-well Plates 1.5 µg/well

|  | RLU/mg mean and s.d. |
|---|---|
| Dotap + LUC | 491,090 |
|  | 142,451 |
| Dotap + ETS | 20,802 |
|  | 2,283 |
| 5 mM ALC + LUC | 18,060 |
|  | 3,241 |
| 5 mM ALC + ETS | 17,025 |
|  | 3,481 |
| 5 mM ALC + dota + LUC | 779,340 |
|  | 159,453 |
| 5 mM ALC + dotap + ETS | 22,411 |
|  | 2,447 |
| 10 mM ALC + LUC | 20,481 |
|  | 7,044 |
| 10 mM ALC + ETS | 17,724 |
|  | 1,020 |
| 10 mM ALC + dotap + LUC | 750,034 |
|  | 94,431 |
| 10 mM ALC + dotap + ETS | 20,520 |
|  | 2.180 |

To verify if the positive effect of ALC on luciferase activity was related to an activation of transcriptional machinery or to an increasing of cell permeability, we decided to quantify the total amount of transfected intracellular plasmidic DNA by Slot blot analysis.

Slot Blot

Cell culture. Cervical carcinoma cell line HeLa (ATCC) were maintained in RPMI medium (Europio) supplemented with 10% foetal calf serum, 1% P/S in a humidified atmosphere with 5% $CO_2$ ALC treatment $5\times10^6$ cells were plated in a 125-cm$^3$ flask and maintained in RPMI, supplemented as described above, containing ALC at two concentrations (5 mM and 10 mM) 4 days before transfection. The treatment was repeated at the end of transfection. Untreated cells were cultured in the same condition and used as control.

Transient Expression of pRL-CMV. $10^5$ cells/well were plated 1 day before transfection in 12 multiwells plate (Corning). DOTAP liposome (Boehringer-Mannheim, Indianapolis, Ind.) and pRL-CMV plasmid (Promega cat. N° E2261) were used for transfection, 6 wells/sample. Briefly, 1.5 µg/well of DNA and a water solution of liposome at 9.2 µM were mixed at room temperature (25 µl/sample) to form DNA-liposome complex. After incubation for 30 min, the same volume/well of HBS 2× (20 mM HEPES, 150 mM NaCl, pH 7.4) was added and the transfection mixture was aliquotated (50 µl/well in supplemented medium). The cells were incubated with the complex for 5 h and the complex removed by washing with PBS (phosphate-buffered saline, pH 7.4, $Ca^{++}$ and $Mg^{++}$ free). Cells were maintained in supplemented medium, containing ALC, for 24h and then used for analysis. Nude DNA in HBS 1× (pRL-CMV) was transfected as control.

DNA extraction. Total cellular DNA was extracted by alkaline lysis from transfected cells according to the method reported by Maniatis. After washing with PBS, cells were collected with PBS (1 ml/well) and centrifuged at 1500×g for 10 min at r.t.

According to protocol, each pellet, placed on ice, was lysed using: 100 µl of solution I [50 mM glucose, 25 mM Tris-HCl (pH=8), 10 mM EDTA (pH=8)], 200 µl of solution II [0.2 N NaOH, 1% SDS], 150 µl of solution III (5M potassium acetate, glacial acetic acid]. After centrifugation at 12000×g for 5 min at 4° C., surnatant was collected and DNA was precipitated with EtOH. Pellet was resuspended in TE 1× (50 µl/sample).

Probe labelling. The probe, the luciferase gene, was obtained by digestion of pRL-CMV with HindIII for 2 h at 37° C. and then with BamHI in the same condition. After digestion, the mixture was electrophoresed on 0.8% agarose gel in TAE 1× buffer (40 mM Tris-HCl (pH 7.8), 1.1 mM EDTA and 37 mM sodium acetate) and the fragment corresponding to luciferase gene was isolated by excision. The labelling of luciferase gene was performed using the Rediprime II DNA labelling system (Amersham Pharmacia biotech, cat n. RPN 1633) and Redivue stabilised [$\alpha$-$^{32}$P] dCTP (Amersham Pharmacia biotech, cat n. AA 0005) according to purchased protocol.

Slot Blot. DNA samples were absorbed on positively charged Nylon membrane (Boehringer, cat. n. 1209299) using Biorad Slot Blot apparatus. The DNA was linked to the filter by U.V. Stratalinker-2400 (Stratagene). After pre-incubation of the filter with QuikHyb Hybridization Solution (Stratagene, cat. n. 201220) for 20 min at 68° C., $2.5\times10^6$ cpm/ml of labelled probe was added, after boiling, with salmon sperm DNA, for 2 min. The hybridization was performed at 68° C. for 1 h, and then the filter was washed twice with buffer I (SSC 2×, SDS 0.1%) for 15 min at room temperature and then with buffer II (SSC 0.1×, SDS 0.1%) for 30 min at 60° C. The filter was exposed to "Phosphor Imager" box and then analysed by densitometry using a IPlab Gel software.

The Slot blot densitometry (see table) revealed that there was no difference between values obtained from transfected cells in presence or absence of ALC. A little decrease was observed with 10, mM ALC. These results showed that the presence of ALC did not change the cellular uptake of the DNA/Liposome complex suggesting that the ALC could affect the expression of luciferase at transcriptional level.

Densitometric Values (Relative Units)

TABLE single values (relative units) obtained by densitometric analysis, using IPlab Gel software, of probed filter shown in the FIGURE. As described above, pRL-CMV DNA was transfected using Dotap (Dotap/DNA complex) and the transfection were performed both in untreated cells (slot 7-12), and treated cells with 5 mM (slot 19-24) and 10 mM (slot 31-36) ALC. pRL-CMV without liposome (nude DNA) was used as controls in the same experimental condition: untreated cells (slot 1-6), treated cells with 5 mM (slot 13-18) and 10 mM (slot 25-30) ALC.

|  | Slot | volume | mean |
|---|---|---|---|
| nude DNA | 1 | 81620 |  |
|  | 2 | 93505 |  |
|  | 3 | 85305 | 72618.2 |
|  | 4 | 64280 |  |
|  | 5 | 56880 |  |
|  | 6 | 54119 |  |
| Dotap/DNA complex | 7 | 239399 |  |
|  | 8 | 250530 |  |
|  | 9 | 251720 | 252088.5 |
|  | 10 | 258812 |  |
|  | 11 | 258100 |  |
|  | 12 | 253970 |  |

TABLE-continued single values (relative units) obtained by densitometric analysis, using IPlab Gel software, of probed filter shown in the FIGURE. As described above, pRL-CMV DNA was transfected using Dotap (Dotap/DNA complex) and the transfection were performed both in untreated cells (slot 7-12), and treated cells with 5 mM (slot 19-24) and 10 mM (slot 31-36) ALC. pRL-CMV without liposome (nude DNA) was used as controls in the same experimental condition: untreated cells (slot 1-6), treated cells with 5 mM (slot 13-18) and 10 mM (slot 25-30) ALC.

|  | Slot | volume | mean |
| --- | --- | --- | --- |
| nude DNA + ALC 5 mM | 13 | 59846 |  |
|  | 14 | 58324 |  |
|  | 15 | 61431 | 61441.5 |
|  | 16 | 70373 |  |
|  | 17 | 63045 |  |
|  | 18 | 55630 |  |
| Dotap/DNA complex + ALC 5 mM | 19 | 222013 |  |
|  | 20 | 255756 |  |
|  | 21 | 253422 | 240634.5 |
|  | 22 | 234654 |  |
|  | 23 | 239053 |  |
|  | 24 | 238909 |  |
| Nude DNA + ALC 10 mM | 25 | 26326 |  |
|  | 26 | 71831 |  |
|  | 27 | 54172 | 52595.2 |
|  | 28 | 70498 |  |
|  | 29 | 48707 |  |
|  | 30 | 44037 |  |
| Dotap/DNA complex + ALC 10 mM | 31 | 173870 |  |
|  | 32 | 225644 |  |
|  | 33 | 116848 | 165345 |
|  | 34 | 114911 |  |
|  | 35 | 157762 |  |
|  | 36 | 203035 |  |

Conclusion. The comparison between densitometric values obtained with transfections performed in presence or absence of ALC reveals that there was no relationship between cellular permeability to DNA/Dotap complex and the positive effect of ALC on luciferase activity.

The invention claimed is:

1. A method for increasing expression of liposome mediated transiently transfected genes in cells comprising the administration of acetyl L-carnitine.

2. A method for increasing in vitro expression of liposome mediated transiently transfected genes in cells comprising the addition of acetyl L-carnitine in the culture medium.

3. A method for the production of recombinant protein by liposome mediated transient transfection comprising the use of acetyl L-carnitine to increase the expression of said recombinant proteins.

* * * * *